United States Patent
Cabiac et al.

(10) Patent No.: US 10,335,772 B2
(45) Date of Patent: Jul. 2, 2019

(54) CATALYST COMPRISING GOLD HOMOGENEOUSLY DISPERSED IN A POROUS SUPPORT

(71) Applicant: IFP Energies Nouvelles, Rueil-Malmaison (FR)

(72) Inventors: Amandine Cabiac, Givors (FR); Antoine Hugon, Givors (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 18 days.

(21) Appl. No.: 15/555,658

(22) PCT Filed: Feb. 9, 2016

(86) PCT No.: PCT/EP2016/052696
§ 371 (c)(1),
(2) Date: Sep. 5, 2017

(87) PCT Pub. No.: WO2016/139034
PCT Pub. Date: Sep. 9, 2016

(65) Prior Publication Data
US 2018/0043337 A1    Feb. 15, 2018

(30) Foreign Application Priority Data

Mar. 5, 2015 (FR) .................... 15 51873

(51) Int. Cl.

| | |
|---|---|
| *B01J 23/52* | (2006.01) |
| *C10G 45/40* | (2006.01) |
| *B01J 37/06* | (2006.01) |
| *B01J 37/10* | (2006.01) |
| *B01J 37/18* | (2006.01) |
| *B01J 35/00* | (2006.01) |
| *B01J 37/02* | (2006.01) |
| *C07C 5/05* | (2006.01) |
| *C07C 7/163* | (2006.01) |
| *B01J 21/04* | (2006.01) |
| *B01J 23/66* | (2006.01) |
| *B01J 35/02* | (2006.01) |
| *B01J 35/08* | (2006.01) |
| *B01J 35/10* | (2006.01) |

(52) U.S. Cl.
CPC ............ *B01J 23/52* (2013.01); *B01J 21/04* (2013.01); *B01J 35/0006* (2013.01); *B01J 35/006* (2013.01); *B01J 35/0013* (2013.01); *B01J 35/0066* (2013.01); *B01J 35/0093* (2013.01); *B01J 37/0201* (2013.01); *B01J 37/0213* (2013.01); *B01J 37/0236* (2013.01); *B01J 37/06* (2013.01); *B01J 37/10* (2013.01); *B01J 37/18* (2013.01); *C07C 5/05* (2013.01); *C07C 7/163* (2013.01); *C10G 45/40* (2013.01); *B01J 23/66* (2013.01); *B01J 35/023* (2013.01); *B01J 35/08* (2013.01); *B01J 35/1009* (2013.01); *B01J 35/1014* (2013.01); *B01J 35/1019* (2013.01); *B01J 35/1038* (2013.01); *B01J 35/1042* (2013.01); *B01J 35/1047* (2013.01); *C07C 2521/04* (2013.01); *C07C 2523/52* (2013.01)

(58) Field of Classification Search
None
See application file for complete search history.

(56) References Cited

U.S. PATENT DOCUMENTS

| | | | | |
|---|---|---|---|---|
| 5,623,090 | A * | 4/1997 | Haruta ............... | B01J 23/52 549/523 |
| 6,602,821 | B2 * | 8/2003 | Petit-Clair ............ | B01J 23/40 502/305 |
| 2010/0010278 | A1 * | 1/2010 | Boyer .................. | C07C 5/09 585/260 |
| 2014/0287912 | A1 * | 9/2014 | Souquet-Grumey .... | B01J 21/18 502/150 |

FOREIGN PATENT DOCUMENTS

| | | |
|---|---|---|
| DE | 10205873 A1 | 8/2003 |
| EP | 709360 A1 | 5/1996 |
| FR | 2932177 A1 | 12/2009 |

OTHER PUBLICATIONS

International Search Report PCT/EP2016/052696 dated Apr. 12, 2016.
Ivanova S et al: "Preparation of alumina supported gold catalysts: Influence of washing procedures, mechanism of particles size growth", Applied Catalysis A: General, Elsevier Science, Amsterdam, NL, vol. 298, Jan. 10, 2006 (Jan. 10, 2006), pp. 57-64, XP028001396, ISSN: 0926-860X, [retrieved on Jan. 10, 2006], DOI: 10.1016/J.APCATA.2005.09.020.
English machine translation of DE10205873A1 published Aug. 21, 2003 to Plzak Vojtech Dr.-Ing. of ZSW.

* cited by examiner

*Primary Examiner* — Melvin C. Mayes
*Assistant Examiner* — Stefanie J Cohen
(74) *Attorney, Agent, or Firm* — Millen, White, Zelano and Branigan, P.C.

(57) ABSTRACT

A catalyst comprising gold and a porous support containing at least one refractory oxide, in which the gold content is in the range 0.01% to 5% by weight with respect to the total weight of catalyst, and in which the particles of gold are distributed homogeneously through said porous support and have a dimension, measured by transmission electron microscopy, in the range 0.5 to 5 nm.

8 Claims, No Drawings

CATALYST COMPRISING GOLD HOMOGENEOUSLY DISPERSED IN A POROUS SUPPORT

TECHNICAL FIELD

The present invention relates to the field of heterogeneous catalysts, and more particularly to supported heterogeneous catalysts comprising gold.

PRIOR ART

Gold, the most noble of metals, was for a long time considered to be catalytically inactive until its catalytic properties were discovered, in particular in the reaction for the oxidation of CO, by preparing the gold in the form of nanoparticles with a dimension of less than approximately 5 nm, supported on reducible oxides (Haruta M. et al, Chemistry Letters, 1987, 2, 405-408 *"Novel gold catalysts for the oxidation of carbon monoxide at a temperature far below 0 degrees ° C."*). Later on, it was discovered that a large number of reactions constitute applications for catalysts based on gold, in particular in selective hydrogenation reactions, the hydrochlorination reaction, the reaction for the conversion of gas using water (also known as the "water-gas shift reaction"), or in fact the production of ethylene oxide and vinyl chloride.

Typically, heterogeneous catalysts comprise at least one metal which may be in the form of small metallic particles deposited on a support, the latter possibly being a refractory oxide. The macroscopic distribution of the metallic particles in the support constitutes an important criterion for catalytic activity and selectivity.

The conventional preparation of heterogeneous catalysts containing gold by dry impregnation of a porous support generally results in a homogeneous distribution of the gold in the shaped solid. However, the particle size of the gold obtained is generally high, of the order of 20 to 30 nm, which results in less active catalysts.

In the context of rapid and consecutive reactions such as selective hydrogenations, the aim is generally to distribute the metallic particles in a shell at the periphery of the support in order to avoid problems with intragranular material transfer which could result in deficiencies in the activity and a loss of selectivity. That type of catalyst is often known as an "eggshell" catalyst.

Thus, the document US2003/232719 discloses a process for the preparation of a catalyst comprising gold for the selective hydrogenation of acetylene. The weight content of gold is in the range 0.05% to 5% by weight with respect to the total weight of catalyst. Approximately 90% by weight of the gold is distributed at the periphery of the support, forming a shell (an eggshell) of approximately 250 micrometers in thickness.

The document US2010/010278 discloses a process for the selective hydrogenation of a light cut (C2) on a fixed bed of catalyst, said catalyst comprising a support and a metallic phase comprising either gold alone or palladium and gold with a gold/palladium molar ratio of more than 5. The catalyst is prepared by adding a solution of a gold precursor to the support then heating it in its entirety to a temperature in the range 60° C. to 100° C. A solution of urea is then added to the solution containing the support and the gold precursor. After adding the urea, stirring of the suspension is maintained, generally for a period in the range 30 minutes to 24 hours at a temperature in the range 60° C. to 100° C. The catalyst precursor obtained is then recovered and washed. The catalyst precursor is then dried and is activated by carrying out a reduction in hydrogen at a temperature in the range 100° C. to 500° C. The catalyst obtained comprises either gold, or gold and palladium, distributed at the periphery of the support thereby forming a shell (eggshell). A preparation by deposition-precipitation with urea as described in that document thus results in the production of particles of gold with small dimensions in an eggshell distribution over the shaped support.

Surprisingly and in contrast to processes of the prior art, the Applicant has established that it is possible to provide a supported catalyst based on gold comprising small particles of gold distributed homogeneously in the porous support (not in the form of an eggshell at the periphery of the support as described in the prior art). These characteristics of the catalyst are in particular obtained by means of a preparation process combining an impregnation of gold followed by a maturation then washing with urea.

The catalyst obtained has improved catalytic properties compared with known catalysts in terms of activity for selective hydrogenation, and more particularly in the selective hydrogenation of light cuts.

Aims of the Invention

In a first aspect, the invention concerns a catalyst comprising gold and a porous support containing at least one refractory oxide, in which the gold content is in the range 0.01% to 5% by weight with respect to the total weight of catalyst, and in which the particles of gold are distributed homogeneously through said porous support and have a dimension, measured by transmission electron microscopy, in the range 0.5 to 5 nm.

Advantageously, the mean particle size of the gold, estimated by transmission electron microscopy, is in the range 0.5 nm to 3 nm, and more preferably less than 3 nm.

Preferably, the metallic dispersion D of the gold is in the range 30% to 100%.

Preferably, the porous support is selected from magnesium oxide, aluminium oxide (alumina), silicon oxide (silica), zirconium oxide, thorium oxide or cerium oxide, taken alone or as a mixture.

Advantageously, said porous support is selected from silica, alumina and silica-alumina.

Preferably, the catalyst comprises a residual chlorine content of less than 200 ppm by weight with respect to the total weight of catalyst.

In another aspect, the invention concerns a process for the preparation of a catalyst in accordance with the invention, said process comprising the following steps:

a) preparing an aqueous solution containing a precursor of gold;

b) impregnating a porous support containing at least one refractory oxide with said solution obtained in step a);

c) maturing the impregnated porous support obtained in step b) in order to obtain a catalyst precursor;

d) bringing the catalyst precursor obtained in step c) into contact with a solution containing urea;

e) drying the catalyst precursor obtained in step d) at a temperature in the range 70° C. to 300° C.

Advantageously, the maturation step is carried out for a period in the range 0.5 to 40 hours.

Preferably, the impregnation step b) is carried out by dry impregnation.

Advantageously, said catalyst precursor is washed between step d) and step e).

Preferably, a step for drying said catalyst precursor obtained in step c) at a temperature in the range 70° C. to 120° C. is carried out between step c) and step d).

Advantageously, the urea/gold molar ratio in step d) is in the range 1 to 1000.

In a particular embodiment, the process in accordance with the invention further comprises a step f) in which the dried catalyst obtained from step e) undergoes a reduction treatment by contact with a reducing gas.

Advantageously, step f) is carried out at a temperature in the range 40° C. to 500° C.

In another aspect, the invention concerns a process for the selective hydrogenation of a C2-C4 cut with a catalyst in accordance with the invention or prepared in accordance with the process of the invention, in which the temperature is in the range 0° C. to 500° C., the pressure is in the range 0.1 to 20 MPa, the hourly space velocity is in the range 0.1 to 50 $h^{-1}$ for a liquid feed, and in the range 500 to 30 000 $h^{-1}$ for a gaseous feed.

DETAILED DESCRIPTION

The groups of chemical elements provided below are given in accordance with the CAS classification (CRC Handbook of Chemistry and Physics, published by CRC press, Editor-in-Chief D. R. Lide, 81st edition, 2000-2001). As an example, the group VIII in the CAS classification corresponds to metals from columns 8, 9 and 10 of the new IUPAC classification.

Catalyst

The invention concerns a catalyst in the form of at least one grain, comprising gold and a porous support containing at least one refractory oxide, in which the gold content is in the range 0.01% to 5% by weight with respect to the total weight of catalyst, preferably in the range 0.02% to 4% by weight, and more preferably in the range 0.02% to 3% by weight, and in which the particles of gold are distributed homogeneously through said porous support and has a dimension, measured by transmission electron microscopy (TEM), in the range 0.5 to 5 nm, preferably less than 4 nm, and more preferably less than 3.5 nm, and yet more preferably less than 3.0 nm, the gold being distributed homogeneously in said grain of porous support.

In accordance with the invention, the term "grain" means the shaped porous support.

The gold is distributed homogeneously in the grain of porous support with a coefficient R (defined in the text below) in the range 0.8 to 1.2.

Advantageously, the specific surface area of the porous support is in the range 1 to 300 $m^2/g$, preferably in the range 2 to 200 $m^2/g$, and more preferably in the range 3 to 150 $m^2/g$.

Advantageously, the residual chlorine content is less than 200 ppm by weight with respect to the total weight of catalyst, preferably less than 100 ppm by weight, and more preferably less than 50 ppm by weight.

Preferably, the dispersion, i.e. the quantity of superficial gold with respect to the total gold introduced, is in the range 30% to 100%, preferably in the range 35% to 100% and highly preferably in the range 38% to 100%. The particle dispersion is a dimensionless number, often expressed as a percentage (%). The dispersion becomes larger as the particles become smaller. It is defined in the publication by R. Van Hardeveld and F. Hartog, "*The statistics of surface atoms and surface sites on metal crystals*", Surface Science 15, 1969, 189-230.

Advantageously, the porous support is selected from magnesium oxide, aluminium oxide (alumina), silicon oxide (silica), zirconium oxide, thorium oxide or cerium oxide, taken alone or as a mixture thereof. Preferably, the porous support is an oxide of aluminium (alumina) or of silicon (silica). More preferably, said support is alumina.

In accordance with the invention, the grain of the porous support is in the form of beads, trilobes, extrudates, pellets or irregular and non-spherical agglomerates the specific shape of which may result from a crushing step. Highly advantageously, said support grain is in the form of beads or extrudates. Yet more advantageously, said support grain is in the form of beads. The grain size of the catalyst is in the range 1 mm to 10 mm, preferably in the range 1.5 to 8 mm.

If the porous support which is selected is formed from alumina, it may equally be in the alpha, delta, theta, chi, gamma, etc crystallographic forms, alone or as a mixture.

The total pore volume of the support is in the range 0.1 to 1.5 $cm^3/g$, preferably in the range 0.2 to 1.4 $cm^3/g$, and more preferably in the range 0.25 to 1.3 $cm^3/g$. The total pore volume is measured by mercury porosimetry in accordance with the ASTM standard D4284-92, with a wetting angle of 140°, for example using an Autopore® III model instrument from Micromeritics®.

The BET specific surface area is measured by nitrogen physisorption. The BET specific surface area is measured by nitrogen physisorption in accordance with ASTM standard D3663-03 as described by Rouquerol F.; Rouquerol J.; Singh K. in "Adsorption by Powders & Porous Solids: Principle, methodology and applications", Academic Press, 1999.

Definition of Coefficient R

The distribution profiles for the elements in the grains of catalyst support are obtained by Castaing microprobe. At least 30 analysis points are recorded along the diameter of the bead or the extrudate. This thereby produces the distribution profile c(x) for x∈[−r;+r], where c is the local concentration of the element, r is the radius of the bead or extrudate and x is the position of the analysis point along the diameter of the grain with respect to the centre of that grain.

The distribution of the elements is characterized by a dimensionless coefficient R which weights the local concentration by a weight which increases as a function of the position on the diameter. By definition:

$$R = \int_{-r}^{r} c(x)x^2 dx \bigg/ \frac{r^2}{3} \int_{-r}^{r} c(x) dx$$

Thus, an element with a uniform concentration has a coefficient R equal to 1, an element deposited in a domed profile (concentration at the core higher than the concentration at the edges of the support) has a coefficient of more than 1 and an element distributed in an eggshell profile (concentration at the edges higher than the concentration at the core of the support) has a coefficient of less than 1. The analysis by Castaing microprobe provides values for the concentrations for a finite number of values of x, and so R is evaluated numerically using integration methods which are well known to the skilled person. Preferably, R is determined using the trapezium method.

Catalyst Preparation Process

The invention also concerns a process for the preparation of the catalyst, comprising the following steps:

a) preparing an aqueous solution containing a precursor of gold;

b) impregnating said porous support with said solution obtained in step a) onto at least one grain of porous support containing at least one refractory oxide, preferably by dry impregnation;

c) maturing said grain of impregnated porous support obtained in step b) in order to obtain a catalyst precursor;

optionally, drying the catalyst precursor obtained in step c) at a temperature in the range 50° C. to 300° C. in air;

d) bringing said catalyst precursor obtained in step c), optionally dried, into contact with a solution containing urea;

optionally, filtering and/or washing the catalyst precursor obtained in step d);

e) drying the catalyst precursor obtained in step d), optionally filtered and/or washed, at a temperature in the range 50° C. to 300° C., in air;

f) optionally, submitting the dried catalyst obtained from step e) to a reduction treatment in a reducing atmosphere (or hydrogen).

In accordance with the invention, the preparation process does not include a non-reducing, thermal oxidizing or neutral heat treatment of the catalyst precursor, in order to avoid the formation of coarse particles of gold (i.e. larger than 5 nm).

a) Preparation of an Impregnation Solution in Aqueous Phase

The solution is prepared by dissolving a gold precursor salt in water.

The precursor salt of gold used has an oxidation state for the metal of more than 0 and is soluble in aqueous solution. The gold precursor salt may be a halide, for example. It may preferably be selected from the group constituted by chlorides of gold, such as gold trichloride, tetrachloroauric acid, sodium or potassium tetrachloraurate. Preferably, the precursor used is tetrachloroauric acid.

In general, the preparation temperature is in the range 5° C. to 40° C. and preferably in the range 15° C. to 35° C. The concentration of gold in the solution is preferably in the range 1 mmol/L to 1 mol/L, i.e. 0.2 g/L to 200 g/L.

b) Deposition of the Solution Prepared in Step a) by Impregnation onto a Support The solution prepared in step a) is then impregnated onto a porous support. The support may be impregnated by dry impregnation, excess impregnation or depleted impregnation, in static or dynamic mode. Dry impregnation is preferred. The impregnation may be carried out in one or more successive impregnation steps.

The dry impregnation step consists of bringing said porous support into contact with at least one solution containing at least one precursor of gold; the volume is equal to the pore volume of said support to be impregnated. This solution contains the metallic gold precursor in the concentration needed in order to obtain the desired final gold content on the catalyst.

The porous support has a specific surface area in the range 1 to 300 m$^2$/g, preferably in the range 2 to 200 m$^2$/g, and more preferably in the range 3 to 150 m$^2$/g.

The porous support may optionally undergo a series of treatments before the impregnation step, such as calcining or hydration steps.

c) Maturation of the Impregnated Porous Support Obtained in Step b)

After impregnation, the impregnated porous support is generally matured for 0.5 to 40 hours, preferably for 1 to 30 hours, preferably at ambient temperature. Preferably, said maturation step is carried out in air and preferably in moist air with a relative humidity in the range 20% to 100%, preferably in the range 70% to 100%.

Optionally, the catalyst precursor may be dried in order to eliminate all or a portion of the water introduced during impregnation, preferably at a temperature in the range 50° C. to 300° C., more preferably in the range 70° C. to 250° C. The drying period is in the range 0.5 h to 20 h. Drying is generally carried out in hydrocarbon combustion air, preferably methane, or in heated air comprising 0 to 80 grams of water per kilogram of combustion air, with an oxygen content in the range 5% to 25% by volume and a carbon dioxide content in the range 0 to 10% by volume.

d) Treatment with Urea

The catalyst precursor obtained in step c), optionally dried, is brought into contact, generally with stirring, with an aqueous solution comprising at least urea.

The volume of the aqueous solution containing at least urea is in the range 1 to 100 times the pore volume of the shaped catalyst. The molar urea/gold ratio is in the range 1 to 1000, preferably in the range 2 to 700, more preferably in the range 3 to 300.

In general, the temperature of the solution is kept constant and is in the range 5° C. to 120° C., preferably in the range 15° C. to 100° C. The dwell time for said aqueous solution in the apparatus is in the range 0.5 to 20 hours.

The urea is diluted in an organic solvent, for example ethanol, and/or an aqueous solvent; preferably, the solvent is water.

The solution containing urea may also contain other organic compounds such as ammonia.

Preferably, the solution contains only urea and water.

Filtration/Washing

Optionally, the catalyst precursor obtained in step d) may be filtered using any technique which is known to the person skilled in the art.

Optionally, the catalyst precursor is washed, preferably with water. The total volume of water engaged for the washing step(s) is in the range 1 to 30 times the catalytic volume engaged. Washing may be carried out in one or more steps. Washing the catalyst precursor means that the urea and/or chlorine present in the catalyst precursor can be eliminated.

The washing period is generally in the range 1 minute to 10 hours, preferably in the range 5 minutes to 8 hours, and more preferably in the range 10 minutes to 7 hours.

e) Drying of Catalyst Precursor Obtained in Step d)

The catalyst precursor is generally dried in order to eliminate all or a portion of the water introduced during impregnation, preferably at a temperature in the range 50° C. to 300° C., more preferably in the range 70° C. to 250° C. The drying period is in the range 0.5 to 20 hours.

Drying is generally carried out in hydrocarbon combustion air, preferably methane, or in heated air comprising 0 to 80 grams of water per kilogram of combustion air, with an oxygen content in the range 5% to 25% by volume and a carbon dioxide content in the range 0 to 10% by volume.

f) Heat Treatment of Dried Catalyst Obtained in Step e) in a Reducing Atmosphere (Optional Step)

Optionally, after drying, the catalyst is generally reduced. This step is preferably carried out in the presence of a reducing gas, either in situ, i.e. in the reactor in which the catalytic transformation is carried out, or ex situ. In general, the reduction temperature is in the range 40° C. to 500° C., preferably in the range from approximately 100° C. to approximately 400° C.

The reduction is carried out in the presence of a reducing gas comprising in the range 25% by volume to 100% by volume of hydrogen, preferably 100% by volume of hydrogen. The hydrogen is optionally supplemented by a gas which is inert as regards reduction, preferably argon, nitrogen or methane. The reduction generally comprises a temperature ramp-up phase followed by a constant temperature stage.

The duration of the constant temperature stage for reduction is generally in the range 0.5 to 10 hours, preferably in the range 2 to 8 hours.

The HSV is generally in the range 150 to 3000, preferably in the range 300 to 1500 liters of reducing gas per hour and per liter of catalyst. The term "HSV" as used in the context of the present invention means the hourly space velocity, defined as the ratio between the volume flow rate of the feed to be treated and the volume of catalyst charged into the reactor. The hourly space velocity is expressed in $h^{-1}$.

The invention also concerns the catalyst obtained from the catalyst preparation process described in the present invention.

Use of the Catalyst in Accordance with the Invention

The catalyst in accordance with the invention may be used in catalytic reactions such as the selective hydrogenation of C2, C3 cuts, C4 cuts, C5 cuts from steam cracking and/or catalytic cracking and gasolines from steam cracking, also known as pyrolysis gasolines, for example.

Preferably, the feeds are C2, C3, C4 cuts from steam cracking and/or catalytic cracking. More preferably, the catalyst in accordance with the invention is used in catalytic reactions for the selective hydrogenation of light cuts (C2-C4).

The selective hydrogenation process has steadily become predominant for the elimination of polyunsaturated compounds from C3 to C5 oil cuts and from pyrolysis gasoline, because this process can convert the most unsaturated compounds into the corresponding alkenes, avoiding total saturation and thus the formation of the corresponding alkanes. Selective hydrogenation may be carried out in the gas or liquid phase, preferably in the liquid phase. In fact, a liquid phase reaction can be used to reduce energy costs and increase the life cycle of the catalysts.

In general, the selective hydrogenation is carried out at a temperature in the range 0° C. to 500° C., a pressure in the range 0.1 to 20 MPa, an hourly space velocity in the range 0.1 to 50 $h^{-1}$ for a liquid feed, in the range 500 to 30000 $h^{-1}$ for a gas feed.

The catalyst in accordance with the invention may also be used in reactions for the oxidation of CO, hydrochlorination, the conversion of gas to water (also known as the "water-gas shift reaction"), and the production of ethylene oxide and vinyl chloride.

Hydrocarbon conversion processes such as steam cracking or catalytic cracking are operated at high temperatures and produce a wide variety of unsaturated molecules such as ethylene, propylene, linear butenes, isobutene, pentenes as well as unsaturated molecules containing up to approximately 15 carbon atoms. At the same time, polyunsaturated compounds are also formed: acetylene, propadiene and methyl acetylene (or propyne), 1,2- and 1,3-butadiene, vinyl acetylene and ethyl acetylene, and other polyunsaturated compounds with a boiling point corresponding to the C5+ gasoline fraction.

All of these polyunsaturated compounds have to be eliminated in order to allow the various cuts to be used in petrochemicals processes such as polymerization units.

EXAMPLES

The examples presented below are intended to demonstrate the improvement in catalytic activity for selective hydrogenation. Examples 1 to 3 concern processes for the preparation of catalysts which are not in accordance with the invention, and Example 4 concerns a process for the preparation of a catalyst.

Example 5 concerns the application of these catalysts to a selective hydrogenation reaction. These examples are presented by way of illustration and do not in any way limit the scope of the invention.

Example 1: Catalyst C1—2% by Weight Au/δ-Al$_2$O$_3$ (not in Accordance with the Invention)

This example demonstrates the conventional preparation of a gold-alumina catalyst by dry impregnation only (and thus without washing with urea).

A stock solution with a concentration of 20 g/L (102 mmol/L) of gold was prepared by diluting two grams of HAuCl$_4$.3H$_2$O with approximately 50 mL of demineralized water, with stirring at 25° C. A portion of this solution was then impregnated onto 20 grams of a delta alumina with a specific surface area of 140 m$^2$/g shaped into the form of beads with a grain size of 2 to 4 mm. A maturation step for 20 hours was carried out on the impregnated support before drying in air in a confined and moist medium. The solid obtained was dried in air for 2 hours at 120° C. The catalyst was then reduced in a stream of hydrogen for 2 hours at 300° C.

The catalyst C1 contained 2% by weight of gold with respect to the total weight of catalyst and 1.6% by weight of chlorine with respect to the total weight of catalyst.

Characterization of the catalyst by Castaing microprobe showed that the gold was distributed homogeneously with a distribution coefficient R (Au)=0.91.

The mean size for the gold particles, measured by transmission electron microscopy, was 30 nm. The corresponding mean dispersion was 4%.

Example 2: Catalyst C2—2% by Weight Au/δ-Al$_2$O$_3$ (not in Accordance with the Invention)

This example demonstrates the preparation of a catalyst by deposition—precipitation, in which the gold and urea were introduced simultaneously in solution as described, for example, in the document FR 2 932 177.

A suspension containing 20 grams of delta alumina support with a specific surface area of 140 m$^2$/g and shaped into the form of beads with a grain size of 2 to 4 mm and 150 mL of water, was placed in a reactor and heated to 80° C. 20 mL of a 20 g/L (102 mmol/L) gold solution was introduced into the reactor. Next, 1.2 grams of urea diluted in 20 mL was then added. The urea/gold molar ratio was 100. The suspension was stirred for 6 hours. The solid was filtered through a Buchner funnel then washed three times with 150 mL of water.

The solid obtained was dried in air for 2 hours at 120° C. The catalyst was then reduced in a stream of hydrogen for 2 hours at 300° C.

The catalyst C2 contained 1.7% by weight of gold with respect to the total weight of catalyst and a chlorine content of less than 0.03% by weight with respect to the total weight of the catalyst.

Characterization of the catalyst C2 by Castaing microprobe showed that the gold was distributed at the periphery of the catalyst with a distribution coefficient R (Au)=0.41.

The mean particle size for the gold, measured by transmission electron microscopy, was 4 nm. The corresponding mean dispersion was 33%.

Example 3: Catalyst C3—2% by Weight Au/δ-Al$_2$O$_3$ (not in Accordance with the Invention)

This example demonstrates the preparation of a catalyst by contact of gold with ammonia (instead of urea) on a delta type alumina.

A stock solution with a concentration of 20 g/L (102 mmol/L) of gold was prepared by diluting two grams of HAuCl$_4$.3H$_2$O with approximately 50 mL of demineralized water, with stirring at 25° C. A portion of this solution was then impregnated onto 20 grams of a delta alumina with a specific surface area of 140 m$^2$/g shaped into the form of beads with a grain size of 2 to 4 mm. The solid was then washed three times with 150 mL of an ammoniacal solution in a concentration of 0.2 mol/L. The solid was then washed with 150 mL of water. A maturation step for 20 hours was carried out on the impregnated support before drying in air in a confined and moist medium. The solid obtained was dried in air for 2 hours at 120° C. The catalyst was then reduced in a stream of hydrogen for 2 hours at 300° C.

The catalyst C3 contained 1.8% by weight of gold and 0.03% by weight of chlorine with respect to the total weight of catalyst.

Characterization of the catalyst by Castaing microprobe showed that the gold was distributed homogeneously with a distribution coefficient R (Au)=0.85.

The mean size for the gold particles, measured by transmission electron microscopy, was 5.3 nm. The corresponding mean dispersion was 23%.

Example 4: Preparation of a Catalyst C4, 2% by Weight Au/δ-Al$_2$O$_3$, in Accordance with the Invention A stock solution with a concentration of 20 g/L (102 mmol/L) of gold was prepared by diluting two grams of HAuCl$_4$.3H$_2$O with approximately 50 mL of demineralized water, with stirring at 25° C. A portion of this solution was then impregnated onto 20 grams of a delta alumina with a specific surface area of 140 m$^2$/g shaped into the form of beads with a grain size of 2-4 mm. A maturation step for 20 hours was carried out on the impregnated support before drying in air in a confined and moist medium. The solid obtained was dried in air for 2 hours at 100° C. The catalyst was then impregnated with a solution of urea in a concentration of 60 g/L. The suspension was stirred at 70° C. for 4 hours. The urea/gold molar ratio was 20. The solid was then filtered and washed 4 times with 150 mL of water. The solid obtained was dried in air for 2 hours at 120° C. The catalyst was then reduced in a stream of hydrogen for 2 hours at 300° C.

The catalyst C4 contained 1.9% by weight of gold and had a chlorine content of less than 0.03% by weight with respect to the total weight of catalyst.

Characterization of the catalyst by Castaing microprobe showed that the gold was distributed homogeneously with a distribution coefficient R (Au)=0.95.

The mean size for the gold particles, measured by transmission electron microscopy, was 2.5 nm. The corresponding mean dispersion was 44%.

Table 1 below summarizes the characteristics of the various catalysts C1 to C4.

TABLE 1

|  | Catalyst | | | |
| --- | --- | --- | --- | --- |
|  | C1 | C2 | C3 | C4 |
| Support | δ-Al$_2$O$_3$ | δ-Al$_2$O$_3$ | δ-Al$_2$O$_3$ | δ-Al$_2$O$_3$ |
| R | 0.91 | 0.41 | 0.85 | 0.95 |
| Size (nm) | 30 | 4.0 | 5.3 | 2.5 |
| Dispersion (%) | 4 | 33 | 23 | 44 |

It will be observed that only a preparation combining an impregnation with a gold precursor, followed by a maturation step, and contact with urea by washing could produce a catalyst comprising particles of gold with small dimensions with a very good dispersion and which are distributed in a homogeneous manner through the grains of the porous support.

Example 5: Selective Hydrogenation

The catalysts C1 to C4 were tested in the selective hydrogenation of butadiene.

A feed comprising 0.3% of butadiene, 30% of butene, 20% of hydrogen and a complement of helium was treated with the catalysts C1, C2, C3 and C4.

Before the reaction, the catalysts C1 to C4 were activated in a stream of pure hydrogen at 300° C. for 2 hours. 100 mg of the catalysts was placed in a tube reactor in downflow mode. The pressure of the reactor was maintained at 0.1 MPa. An hourly space velocity (GHSV) of 30000 h$^{-1}$ was applied. The composition of the feed and of the effluent were measured continuously at the reactor outlet by gas phase chromatography.

The performances were expressed as the temperature T1, defined as the temperature necessary to obtain a butadiene conversion of 98%. The temperatures T1 of the catalysts C1 to C4 are reported in Table 2 (below).

TABLE 2

| Catalyst | Temperature T1 (° C.) |
| --- | --- |
| C1 (not in accordance) | 270 |
| C2 (not in accordance) | 168 |
| C3 (not in accordance) | 176 |
| C4 (in accordance) | 159 |

The catalyst C4, in accordance with the invention, was more active than the catalysts C1, C2 and C3.

The invention claimed is:

1. A process for the preparation of a catalyst wherein the catalyst comprises particles of gold and a porous support containing at least one refractory oxide, in which a content of the particles of gold is in the range of 0.01% to 5% by weight with respect to the total weight of the catalyst, and in which the particles of gold are distributed homogeneously through said porous support and have a dimension, measured by transmission electron microscopy, in the range of 0.5 to 5 nm wherein said process comprising the following steps:
   a) preparing an aqueous solution containing a precursor of the particles of gold;
   b) impregnating the porous support containing the at least one refractory oxide with said solution obtained in step a)
   c) maturing the impregnated porous support obtained in step b) in order to obtain a catalyst precursor;

d) bringing the catalyst precursor obtained in step c) into contact with a solution containing urea;

e) drying the catalyst precursor obtained in step d) at a temperature in the range of 70° C. to 300° C. to obtain the catalyst.

2. The process as claimed in claim 1, characterized in that the maturation step is carried out for a period in the range 0.5 to 40 hours.

3. The process as claimed in claim 1, characterized in that the impregnation step b) is carried out by dry impregnation.

4. The process as claimed in claim 1, characterized in that said catalyst precursor is washed between step d) and step e).

5. The process as claimed in claim 1, characterized in that a step for drying said catalyst precursor obtained in step c) at a temperature in the range 70° C. to 120° C. is carried out between step c) and step d).

6. The process as claimed in claim 1, characterized in that the urea/gold molar ratio in step d) is in the range 1 to 1000.

7. The process as claimed in claim 1, characterized in that it further comprises a step f) in which the dried catalyst obtained from step e) undergoes a reduction treatment by contact with a reducing gas.

8. The process as claimed in claim 7, characterized in that the step f) is carried out at a temperature in the range 40° C. to 500° C.

* * * * *